(12) United States Patent
Samburski et al.

(10) Patent No.: US 11,364,505 B2
(45) Date of Patent: Jun. 21, 2022

(54) POWDERIZED CANNABIS AND USES THEREOF

(71) Applicant: FINE-CAN LTD, Ein Vered (IL)

(72) Inventors: Guy Samburski, Beit-Yitzhak (IL); Yan Beliavsky, Ma'alot-Tarshiha (IL)

(73) Assignee: FINE—CAN LTD, Ein Vered (IL)

( * ) Notice: Subject to any disclaimer, the term of this patent is extended or adjusted under 35 U.S.C. 154(b) by 0 days.

(21) Appl. No.: 17/385,949

(22) Filed: Jul. 27, 2021

(65) Prior Publication Data

US 2022/0126303 A1    Apr. 28, 2022

(51) Int. Cl.
| | |
|---|---|
| B02C 19/06 | (2006.01) |
| B02C 23/20 | (2006.01) |
| B02C 25/00 | (2006.01) |
| B02C 21/00 | (2006.01) |
| B02C 23/00 | (2006.01) |
| B01D 11/02 | (2006.01) |

(52) U.S. Cl.
CPC .............. *B02C 23/20* (2013.01); *B02C 19/06* (2013.01); *B02C 19/061* (2013.01); *B02C 21/00* (2013.01); *B02C 23/00* (2013.01); *B02C 25/00* (2013.01); *B01D 11/0288* (2013.01)

(58) Field of Classification Search
CPC ......... B02C 23/00; B02C 23/20; B02C 19/06; B02C 19/061
See application file for complete search history.

(56) References Cited

U.S. PATENT DOCUMENTS

| | | | |
|---|---|---|---|
| 5,855,326 A * | 1/1999 | Beliavsky | B02C 19/061 241/5 |
| 6,789,756 B2 * | 9/2004 | Beliavsky | B02C 19/061 241/5 |
| 10,052,636 B2 * | 8/2018 | Bates | B02C 23/10 |
| 10,213,788 B2 * | 2/2019 | Bates | A61K 36/185 |
| 10,619,102 B2 * | 4/2020 | Sunderland | C08K 3/04 |
| 10,639,640 B2 * | 5/2020 | Nahtigal | B02C 23/14 |
| 10,780,442 B2 * | 9/2020 | Pal | B01D 11/028 |
| 10,857,101 B1 * | 12/2020 | Millikin | A61Q 19/00 |
| 10,913,900 B2 * | 2/2021 | Sunderland | B02C 17/186 |

(Continued)

FOREIGN PATENT DOCUMENTS

WO    2019/153083 A1    8/2019

OTHER PUBLICATIONS

"Superfine Vortex mill", retrieved from the internet: URL: <https://web.archive.org/web/20201001162515/https://www.superfinemicro.com/unique-technology>,(retrieved on Jan. 4, 2021), Oct. 1, 2020 (Oct. 1, 2020).

(Continued)

*Primary Examiner* — Faye Francis
(74) *Attorney, Agent, or Firm* — Soroker Agmon Nordman (57) ABSTRACT

There is provided a method for enhanced extraction of cannabis oil from a cannabis plant material, and a free-flowing powder consisting of particles of cannabis plant material for use in such method. The cannabis plant material is characterized by a cannabis strain and a cannabis plant part. The method including a step of comminuting the cannabis plant material to a powder of a preselected particle size distribution (PSD) characterized by $10 \leq Dv(90) \leq 100\,\mu m$ as determined by laser diffraction particle size analysis prior to the extraction process, whereby the PSD is preselected in accordance with cannabis strain and the plant part.

12 Claims, 2 Drawing Sheets

(56) References Cited

U.S. PATENT DOCUMENTS

| | | |
|---|---|---|
| 11,000,856 B2 * | 5/2021 | Pal ............................ B07B 1/22 |
| 11,040,932 B2 * | 6/2021 | Smeltzer .................. B01J 21/16 |
| 11,084,770 B2 * | 8/2021 | Black ...................... G01N 30/02 |
| 11,179,757 B2 * | 11/2021 | Lee ........................... B09B 5/00 |
| 11,202,771 B2 * | 12/2021 | Black .................. A61K 36/185 |
| 2007/0072939 A1 | 3/2007 | Kupper |
| 2008/0305236 A1 * | 12/2008 | Tatarliov ................ A21D 13/04 |
| | | 426/590 |
| 2017/0202896 A1 * | 7/2017 | Hugh .................. A61K 31/352 |
| 2018/0304274 A1 * | 10/2018 | Bates ........................ D01B 9/00 |
| 2019/0176161 A1 * | 6/2019 | Beliavsky ............. B02C 19/061 |
| 2020/0206151 A1 | 7/2020 | Whittle et al. |
| 2020/0221644 A1 * | 7/2020 | Nahtigal ................ A01G 3/002 |
| 2020/0289595 A1 | 9/2020 | Platt et al. |
| 2020/0323937 A1 | 10/2020 | Ochs |
| 2021/0114038 A1 * | 4/2021 | Sandnes ................. A23N 15/02 |
| 2021/0163824 A1 * | 6/2021 | Sunderland ............. B02C 23/12 |

OTHER PUBLICATIONS

Effect of Size Reduction Parameters in Pharmaceutical Manufacturing Process, Brian Breneman, Abbott Laboratories, 2011.
Cosmetics Andtoiletries vol. 135, No. 8 | Sep. 2020.
Extraction Efficiencies for Butane, CO2, and Ethanol—Aug. 23, 2019 by Petar Petrov.
Extraction Solvents—Jan. 10, 2019 by Tamir Bresler.
The cannabis Science—Optimization of cannabis extraction yield by controlled milling—Aug. 2017.

* cited by examiner

POWDERIZED CANNABIS AND USES THEREOF

TECHNICAL FIELD

The present invention generally relates to cannabis processing. More specifically, the invention relates to free-flowing fine powders of cannabis plant material. The invention further relates to a method for preparing such powders and to uses thereof.

BACKGROUND

In recent years, the study of cannabis for medical applications has been rapidly growing with new indications and territories of use added at high pace. Cannabis has been shown to provide relief and relaxation for a variety of symptoms and conditions, including chronic and acute pain, nausea and vomiting, appetite loss, neurological conditions, chronic inflammation and more. The wide range of potential therapeutic effects of cannabis are attribute to the extensive profile of cannabinoids, terpenes and flevanoids, which act on cannabinoids receptors, also known as the human endocannabinoid system.

More than 100 different cannabinoids have been isolated from cannabis plant material. The amount and composition of the cannabinoids vary from one strain of cannabis plant to another, within different parts of the plant, and may also depend on the growing conditions of the plant. The most abundant cannabinoids present in cannabis are tetrahydrocannabinol (THC) and cannabidiol (CBD). In the cannabis plant they are produced in their carboxylic acid forms tetrahydrocannabinolic acid (THCA) and cannabidiolic acid (CBDA), respectively, and are decarboxylated by heating (e.g., smoking or baking), by light, or by natural degradation. There is a wide range of cannabis strains that have been selectively bred to produce different levels of THC and CBD and different THC to CBD ratios. Thus, it is possible to choose a Cannabis variety to or to mix two of more different varieties in order to produce a material with the preferred cannabinoid ratio for formulating into a pharmaceutical formulation. The main source for THC and CBD are the upper (aerial) parts of the cannabis plant, in particular the budding heads.

Medical cannabis can be used as a whole-plant product by inhalation via smoking or via vaporization, by ingestion of edible products or by applying it topically on the skin.

However, many of the medical applications of cannabis are based on cannabis extract, or cannabis oil, which contains a mix of cannabinoids. The extracted oil can be administered as is or can be formulated with other ingredients and/or carriers to produce cannabis products such as a gelatin capsule, edible oil, a cream, an ointment, etc. Alternatively, the extracted oil may be further processed to isolate a single cannabinoid or blends of cannabinoids for desired uses. The oil can be extracted from different parts or tissues of the cannabis plant. The two main parts of the plant that are used for extracting cannabis oil are the flower buds and the trim, which is the by-product of trimming the flower buds.

Typically, cannabis oil is extracted from cannabis plant material by extraction with organic solvents. Typical solvent extraction processes involves contacting the plant material with the solvents, using pressurized vessels, or using specific extraction equipment such as an extraction centrifuge. The organic solvent may be a nonpolar solvent such as butane and supercritical $CO_2$ or a polar solvent such as lower alkyl alcohols, e.g., methanol and ethanol. The most common solvent in use for cannabis extraction is ethanol. However, the yield of typical solvent extraction is relatively low, typically of no more than 80% of the compounds being extracted. This leads to losses, higher processing costs and higher price of the product to the patient.

With the expansion of legalization of medical cannabis to an increasing number of countries, there is a continuously growing demand for cannabis and cannabis-based medicinal products. There is therefore an ongoing need for new and improved methods for processing cannabis to better exploit the benefits thereof. Such methods should address both the production of whole-plant cannabis products as well as the extraction of cannabis components, in particular cannabinoids, for the production of cannabis-derived products.

There is also a need for enhancing the extraction efficiency and yield of cannabinoids from cannabis raw material, for extracting more oil from a given quantity of raw material and for producing cannabis oil richer in active compounds. In particular, given that ethanol is the most common solvent used in extraction, there is a need for increasing efficiency and yield of ethanolic extraction of cannabis.

The present invention provides for a free-flowing powder of cannabis plant material that can be incorporated as-is in medical formulations or can be used as the starting material for enhanced extraction of cannabinoids and/or other cannabis components that can be utilized in the production of cannabis-based pharmaceutical products. It will be appreciated that the flowability of a powder is of critical importance in production of pharmaceutical products.

SUMMARY

One aspect of the present invention relates to fine free-flowing powders of consisting of particles of cannabis plant material, wherein the powder has a preselected particle size distribution (PSD) characterized by $Dv(90) \leq 500$ μm determined by laser diffraction particle size analysis. The cannabis plant material can be a fresh cannabis plant material, a decarboxylized cannabis plant material or a dry cannabis plant material. The cannabis plant material may be any part or combination of parts of the cannabis plant, including cannabis flowers, leaves, trim, etc.

In accordance with some embodiments of the invention, the preselected PSD is characterized by $Dv(90) \leq 100$ μm, $Dv(50) \leq 20$ μm and $Dv(10) \leq$ μm. In accordance with other embodiments, the preselected PSD may be characterized by $Dv(90)$ in the range of 20 to 80 μm and $Dv(10) \geq 5$ μm or by $d_{90} \leq 5$ μm.

In accordance with some embodiments of the invention, the free-flowing powder is prepared by subjecting particles of said cannabis plant material to flow regime comprising a vortex flow and controlled changes in air pressure and flow direction of said vortex flow such that the particles of the cannabis plant material break along internal cavities. The cannabis plant material may be shredded to pieces of 1-10 mm size prior to subjecting to the flow regime. In accordance with an embodiment of the invention, the powder is prepared in a vortex mill such a SuperFine Vortex mill.

The free-flowing powders of the invention may be used for extraction of cannabis oil, wherein said PSD is preselected in accordance with the strain and plant part comprising the cannabis plant material and with extracting solvent to obtain maximal cannabinoids extraction or to meet specific requirements of a desired extract composition.

A further aspect of the invention relates to pharmaceutical or cosmetic compositions comprising or consisting of the micronized powders of cannabis plant material. The pharmaceutical composition may be formulated for oral administering, for topical administering or for administering by inhalation and may be in the form of a tablet, capsule, sachet, cachet, lollipop, lozenge, film, dermatology cream, ointment, nasal formulation, inhalable formulation, cosmetic face mask, soap, a toothpaste, etc.

Another aspect of the invention relates to a method for making fine free-flowing powders of cannabis plant material having a particle size distribution (PSD) characterized by Dv(90)·500 µm. The method comprises shredding cannabis plant material to obtain coarse powder comprising particles of about 1-10 mm in size; feeding the coarse powder to a vortex mill; and subjecting the coarse powder to aerodynamic forces comprising a vortex flow and rapid perturbations in air pressure while controlling the milling energy, the residence time of the particles inside the vortex mill and the cut-off by setting the operation parameters of the vortex mill, such that only particles with said PSD exit the mill. The operation parameters of the vortex mill are one or more of the following: air pressure, feeding rate, flow rate and the geometry of the vortex cell. The PSD is preselected according to intended use of said powder.

Yet, a further aspect of the invention is an improved method for extracting cannabis oil and/or cannabis active components from cannabis plant material. The method comprises comminuting the cannabis plant material to a powder prior to extraction, wherein the powder has a preselected particle size distribution (PSD) characterized by Dv(90)≤500 µm and wherein the PSD is preselected in accordance with the strain and plant part of the cannabis plant material and in accordance with the extracting solvent, in order to obtain maximal cannabinoids extraction or to meet specific requirements of the desired extract composition.

Other features and advantages of the invention will be apparent from the following detailed description.

BRIEF DESCRIPTION OF THE DRAWINGS

The present invention will be understood and appreciated more fully from the following detailed description taken in conjunction with the drawings in which.

DETAILED DESCRIPTION

It will be appreciated that the preferred methods, uses, materials, and examples that are described in the following, are illustrative only and are not intended to be limiting. Materials, uses and methods similar or equivalent to those described herein can be used in practice or testing of the invention.

The present invention provides for a fine free-flowing cannabis powder of a preselected particle size distribution (PSD) and for a method for making the same. Preferably, the powders of the invention are characterized by a PSD of Dv(90)≤500 µm, where the parameter Dv(90), also known as d(90), d(0.9) or $d_{90}$, signifies that 90% of the particles in the powder have a size smaller than the value of Dv(90). Similarly, $d_{10}$ means that 10% of the particles have a size smaller than the value of Dv(10) and Dv(50) signifies the median. One of the commonly acceptable technologies for quantitative assessing the above mentioned parameters is based on light scattering or laser diffraction.

The free-flowing cannabis powder of the invention can be used as-is in pharmaceutical formulations or can be processed further for oil extraction. Optionally, decarboxylation may be performed before or after micronization). When preparing the powder, the PSD can be preselected according to intended use. It will be appreciated that the particle size and the particle size distribution may significantly influence pharmaceutical and biological properties, such as, for example, bioavailability.

As is generally known in the pharmaceutical field, powders characterized by $d_{90}$≤1000 µm are commonly used for general powder formulation, such as sachets, capsules or tablets; powders characterized by $d_{90}$≤20 µm are commonly used for dermatological preparations or special formulations; and powders characterized by $d_{90}$≤5 µm are commonly used for inhalable dose forms.

Fine, free-flowing powders of cannabis plant material are not known in the industry. Moreover, since the plant is of natural origin, rich in moisture and oil, it is not available as a free-flowing powder maintaining the same properties (e.g. moisture) as the original whole plant material. As is well known in the art, fine milling technologies require the material to be very dry before milling. Preferably the powders of the invention contain substantially all of the cannabinoids naturally present in the plant and most of the water content.

Conventional methods include milling or shredding of the cannabis plant material by mechanical mills or shredders. Typical conventional machines include hammer mills, cone mills, mechanical sieves or designated shredders, or cutting mills such as the Fritsch Pulverisette 19. However, none of these technologies are capable of producing powder fine enough as described above. Typical powder obtained by these methods would consist of particles of 1 mm (1000 microns) or more, which is 10-100 times larger than required for pharmaceutical formulation or for efficient extraction. Furthermore, more aggressive conventional milling technologies, such as pin-mill, impact mills, air-classifying mills and air jet mills cannot be applied for this purpose in an efficient way. Feeding plant parts would result in clogging, sticking and agglomeration of the particles, resulting in a poor quality, non-powdery substance.

The novel cannabis powders of the present invention are made by comminuting cannabis plant material by a 'soft milling' process that involves only aerodynamic forces, where reducing the particles size is mainly due to subjecting the particles to rapid changes in air pressure. The rapid changes in the air pressure induce rapid internal pressure changes in natural internal cavities within the particles, resulting in the particles breaking down from within-out. Such a process can be combined with a vortex flow that carries suspended particles within a vortex cell while subjecting them to rapid changes of air pressure, as is done, for example, in the vortex mills distributed by SuperFine LTD., Israel. Vortex mills suitable for implementing the preset invention are described, for example, in U.S. Pat. Nos. 5,855,326 and 6,789,756 and in US publication No. 2019/0176161, the entire contents of which are incorporated herein by reference.

It was surprisingly found that comminuting cannabis plant material in a SuperFine Vortex mill produces a fine free flowing powder in an efficient way. The SuperFine mill includes a vortex chamber fed by pressurized air. Upon feeding cannabis plant particles of about 1-10 mm in size into the vortex chamber, the particles are subjected to rapid alternating air pressures that induce a soft milling process upon the particles. The result is a free-flowing powder of a preselected PSD produced in high capacity and good yield. The mill enables tight control over PSD by regulating the milling energy and the residence time of particles inside the vortex chamber and by setting the cut-off PSD, i.e. the maximal PSD that can exit the mill. These values are set by the internal geometry of the mill (which can be easily changed between several options), the feed rate and the air pressure.

Figure 1:
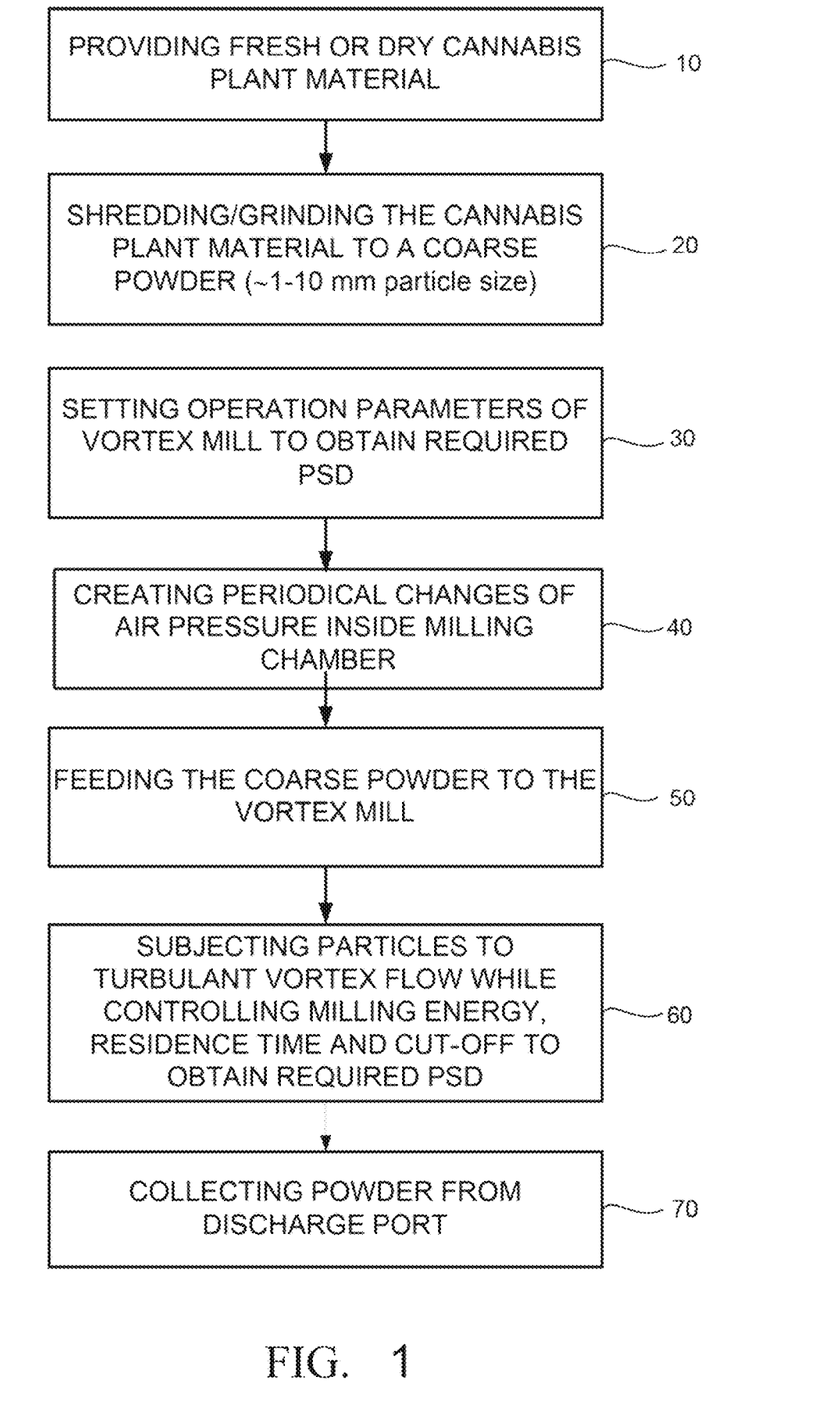
FIG. 1 is a flow chart of a method of making cannabis powder according to an embodiment of the present invention.

The process of making the powders of the invention is outlined in FIG. 1. In accordance with the present invention, the raw cannabis plant material to be processed may be either fresh or dry plant material (10). It may be a whole plant material or may be collected from specific part (e.g., buds, leaves, stalks, roots, seeds, etc.) or combination of parts of the cannabis plant. In accordance with some embodiments, the plant material may be a mixture of plant material from cannabis plants of different strains. It will be realized that the specific composition of the powder (in terms of cannabinoids and/or other ingredients) may be tailored to intended use by combining different strains and/or plant parts.

The raw material is first ground or shredded to coarse particles of about 1-10 mm size (20). This initial grinding can be done in any conventional mill or grinder. The coarse powder is fed into a vortex mill (50) after setting the operation parameters of the mill to obtain the required PSD (30) and creating periodical changes of the air pressure inside the milling chamber (40). The operation parameters of the vortex mill include the air pressure and flow rate of the working flow, the feeding rate of the plant material and the geometry of the vortex cell. These parameters control the milling energy, the residence time the particles spend inside the milling chamber and the cut-off (i.e., the maximal size of the particles exiting the vortex chamber), which collectively determine the PSD of the fine powder. Control over the milling energy is achieved regulating the air pressure and flow rate of the working flow while control over the residence time and the cutoff is achieved by regulating the feeding rate and the geometry of the vortex cell cut-off (e.g., by mechanical elements, an insert sieve). Inside the milling chamber, the particles are subjected to a turbulent vortex flow regime comprising rapid changes in the pressure and direction of the working flow while controlling the milling energy, the residence time and the cut-off (60) such that a powder of the required PSD is discharged through and collected from the discharge port of the mill (70).

It will be realized that although, for simplicity sake, steps 30 to 70 are depicted in FIG. 1 in sequential manner, in practice they may be performed in different order or one or more steps may be performed simultaneously. Thus, coarse powder can be continuously fed into the mill to be processed therein while the fine/micronized powder is continuously collected from the discharge port.

The micronized material so obtained is a uniform free flowing powder, i.e., it does not visually appear to contain any significant quantities of agglomerates, is not sticky, has no or hardly any tendency to aggregate or to adhere to contact surfaces and can be poured from one vessel to another.

Figure 2:
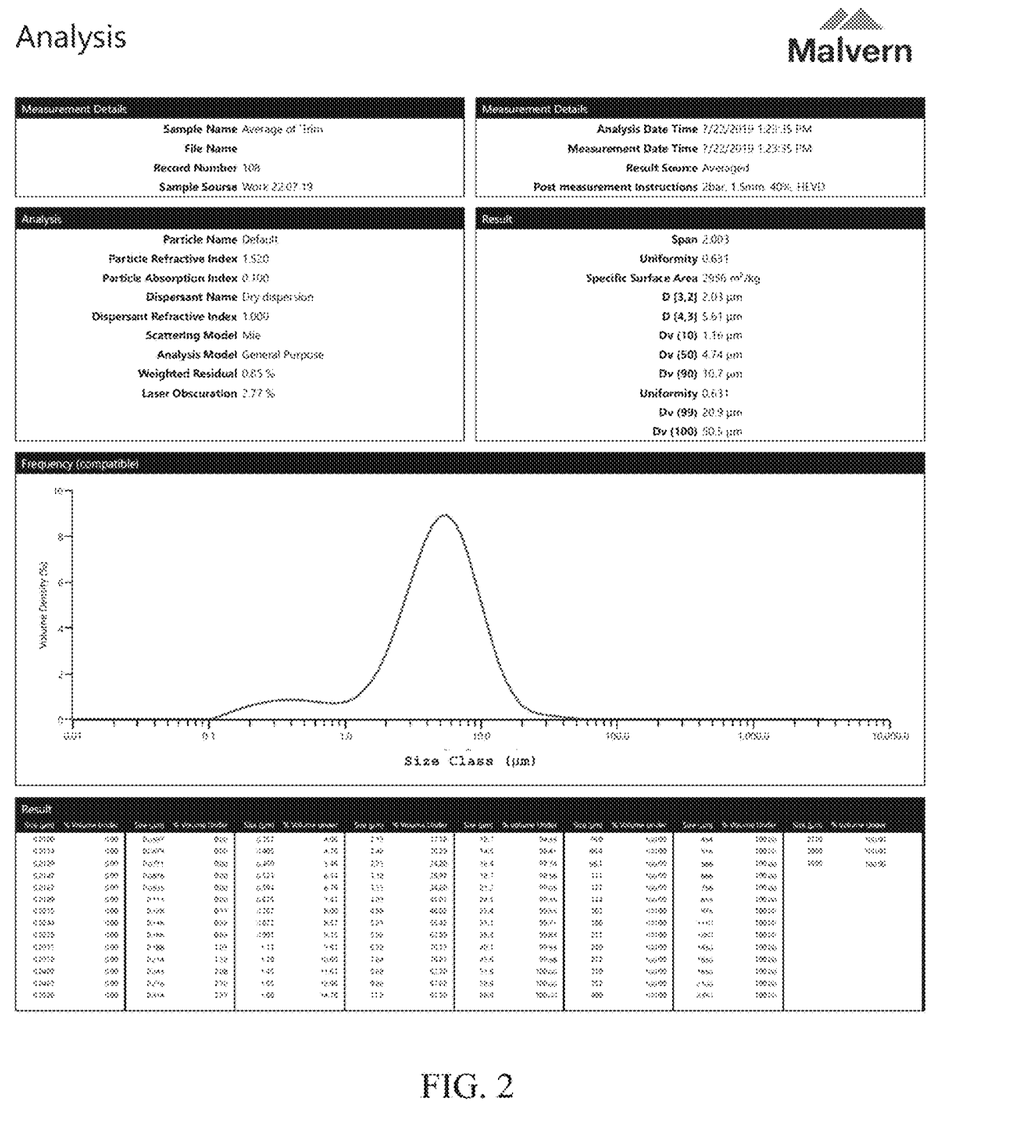
FIG. 2 is an example of a particle size distribution of a typical cannabis powder of the invention.

FIG. 2 presents an example of particle size distribution of a typical cannabis powder of the invention (cannabis trim) prepared according to the method described in FIG. 1. The analysis results shown in FIG. 2 were obtained by laser diffraction particle size analyzer (Mastersizer 3000 manufactured by Malvern Instruments Company).

The powders of the invention are also characterized by being consisting of particles that result from disintegration and destruction of the cellular structures (walls and membranes) of the plant material, i.e., destruction of the internal barriers of the plant material, thus enhancing exposure and release of the active ingredients (e.g., cannabinoids). In this respect, the powders of the invention can be considered as cannabis powders with enhanced activity and/or bioavailability.

It was also discovered that milling the plant parts to a fine powder significantly enhances the amount of active compounds (e.g., cannabinoids) being extracted by the standard methods. Furthermore, it was surprisingly and unexpectedly discovered that there is an optimal particle size range of powder in which the extraction is mostly efficient. In was found that below a certain particle size there is no further increase in extractability and in certain cases even a decrease in extractability was observed. Without wishing to be held to any one theory, it is currently believed that unlike conventional milling, the present approach is not based on obvious surface area increase, but rather on disintegrating fibers, cells and membranes of the plant by a unique mechanism. Apparently, once disintegration is complete, there is no effect in further size reduction. This may be due to over-destruction of cells, molecular degradation etc. For the sake of simplicity, the optimal range of particle size for cannabinoids extraction is described in terms of $d_{90}$. This range was found to be between 10 and 100 microns and may be further narrowed according to a specific plant strain or plant part being extracted. In different cases it was found that the optimal size would be approximately between 13 and 100 microns, 24 and 100 microns, or between 50 and 100 microns.

The powders of the invention can be prepared from whole plants or from any part or combination of parts of the cannabis plant. Preferably, the powders are made from those parts that are rich in cannabinoids, i.e. the upper parts of the plant, in particular the budding/flowers heads that are covered with trichomes rich in cannabinoids. The budding/flowers head of the cannabis includes both inflorescences and leaves. In the context of the present application, the terms flowers, buds and flower buds refer interchangeably to the inflorescences part of the budding head after removal of the leaves (trimming). The term trim refers to the by-product of trimming the budding head, and typically includes a mix of sugar leaves (leaves covered by trichomes) and fan leaves.

The term "fine powder" is used herein to describe powders characterized by $d_{90} \leq 1000$ μm. The term "micronized powder" is used herein in a non-limiting way to describe powders characterized by $d_{90} \leq 100$ μm.

Preferably, cannabis powders characterized by $d_{90} \leq 1000$ μm may be used for general powder formulation, such as sachets, capsules or tablets; powders characterized by $d_{90} \leq 100$ μm, preferably in the range of 20-80 μm, may be used for extraction; powders characterized by $d_{90} \leq 20$ μm may be used for dermatological preparations or special formulations; and powders characterized by $d_{90} \leq 5$ μm may be used for inhalable dose forms.

The following non-limiting examples further illustrate the present invention. It will be appreciated that the free-flowing cannabis powders of the present invention can be prepared from fresh cannabis material (e.g., flowers, trim), as demonstrated in the following examples, with no need to dry the plant material prior to milling, thus saving time, equipment and costs associated with drying processes. However, it will be easily realized that when a dry and/or decarboxylated powder is required, drying and/or decarboxylation can be performed by any known method either before or after milling.

Example 1

Preparation of Cannabis Trim Powder

Cannabis trim from four different cannabis strains were supplied tested:
THC rich #1—from grower #1
THC rich #2—from grower #2
THC rich #3—from grower #2
Balanced CBD and THC #4—from grower #2
Trim was obtained by a trimming machine that separates flowers from the surrounding leaves. In the trimming process, the flower is rolled on a screen and a moving knife is cutting any parts of the flower (mainly sugar and fan leaves) protruding through the screen. The trim contains a mix of sugar (the small leaves covered with trichomes) and fan leaves. The content depends on the shape of the flower and size of leaves, both highly varying among species. The cannabis trim from each strain was sieved in 5 mm mesh to produce particles of up to 5 mm in size.

The shredded trim was then fed by vacuum to a Superfine Vortex mill (model: Superfine SF 90). The mill was operated using air pressures of 2.5-6 bars and feed-rate of 0.667-3.77 kg/hr with additional air supply assisting the flow. The product contact material is stainless steel. By varying the milling parameters (e.g., geometry of internal inserts, feed rate and air pressure) a wide range of powders was obtained for each of the stains.

Particle size distribution was measured with Malvern Mastersizer 3000 using Dry dispersion. The reported values were d(0.1), d(0.5) and d(0.9) expressed in microns (μm). In the following Examples, the value of d(0.9) is used to describe the PSD of the samples.

Example 2

The Effect of Particle Size on Cannabinoids Extractability from Trim of THC-Rich Cannabis Strains Samples of the THC-rich powders obtained as described in Example 1 were extracted in methanol. Following extraction, the content of the active compounds THCA-A and $\Delta^9$-THC was analyzed using a HPLC-PDA-MS instrument. The amount of total cannabinoid compounds was also measured.

Analysis was performed in a certified Cannabinoid lab, following the American herbal pharmacopeia monograph. 100 mg samples of cannabis trim powder of different PSD were dispersed each in 10 ml methanol and vortexed for about 5 seconds. Then the samples were sonicated for 30 minutes at 35° C. After sonication, the mixture was vortexed for 5 seconds and the solution was set to cool dawn for 10 minutes at room temperature, followed by 5 seconds vortexing, filtration and directly injected to the UPLC-PDA-MS.

The following cannabinoids were scanned and quantified (CBDVA, CBDV, CBDA, CBGA, CBD, CBG, THCV, THCVA, CBN, D9-THC, D8-THC, CBL, CBC, THC-A and CBCA).

UPLC-PDA-MS: Column packing/dimension: ACQUITY UPLC BEH C18, (150×2.1 mm, 1.7 μm); Pre-column/dimension: ACQUITY UPLC BEH C18 VanGuard, (5×2.1 mm, 1.7 μm); Mobile phase: Linear gradient conditions was used that includes: A: Water, 5 mM ammonium formate, 0.1% formic acid (FA) and B: Acetonitrile, 0.1% formic acid (FA); Flow rate: 0.5 mL/min; Detectors PDA: at 228 nm; MS: Full scan-ESi in the positive & negative modes with mass range of 200-500 Da.; Injection volume 2 μL; Column temperature: 35° C.; Vial temperature 25° C.

THC Rich #1

The results obtained for 12 samples of THC-rich #1, with dv(0.9) ranging between 5.7 and 92.4 microns are presented in table 1. Corresponding values of $d_v(0.5)$ and $d_v(0.1)$ are also presents for each sample. The first three columns are the HPLC results for the two main peaks of the HPLC results. The last three columns describe the improvement as compared to the un-micronized reference material.

TABLE 1

The effect of particle size on cannabinoids extractability TCH rich #1

| $d_{90}/d_{50}/d_{10}$ microns | THCA-A (wt/wt) %* | $\Delta^9$-THC (wt/wt) %* | Total Cannabinoids % (wt/wt) | THCA-A (improve) % | $\Delta^9$-THC (improve) % | Total (improve) % |
|---|---|---|---|---|---|---|
| Original trim (about 3000 microns) | 4.8 | 0.74 | 7.09 | | | |
| 92.4/18.7/3.8 | 5.39 | 0.93 | 8.02 | 12.3 | 25.7 | 13.1 |
| 77.7/16.9/3.8 | 5.61 | 0.98 | 8.39 | 16.9 | 32.4 | 18.3 |
| 52.1/11.5/2.8 | 5.53 | 0.98 | 8.16 | 15.2 | 32.4 | 15.1 |
| 49/12.1/2.9 | 5.96 | 1.04 | 8.84 | 24.2 | 40.5 | 24.7 |
| 38.2/10/2.8 | 5.82 | 1.03 | 8.83 | 21.3 | 39.2 | 24.5 |
| 29.2/8.7/2.2 | 6.13 | 1.08 | 9.06 | 27.7 | 45.9 | 27.8 |
| 24/8.4/2.33 | 6.14 | 1.02 | 8.96 | 27.9 | 37.8 | 26.4 |
| 13.4/5.27/1.1 | 6.61 | 0.95 | 9.44 | 37.7 | 28.4 | 33.1 |
| 10.7/4.7/1.1 | 5.91 | 1.02 | 8.78 | 23.1 | 37.8 | 23.8 |
| 10.7/4.74/1.16 | 5.87 | 1.02 | 8.72 | 22.3 | 37.8 | 23.0 |
| 7.4/3.4/0.46 | 5.14 | 0.75 | 7.51 | 7.1 | 1.4 | 5.9 |
| 5.7/2.81/0.38 | 4.92 | 0.72 | 7.22 | 2.5 | −2.7 | 1.8 |

*% wt/wt of cannabinoid in sample

It can be seen that all micronized samples show significant increase in Cannabinoids yield compared to the untreated sample. The increase is by 8-39%. It can also be seen that for all compounds, a decrease of extractability occurs when samples are micronized to a value of dv(0.9) under 10 microns.

As can also be seen, there is an optimal PSD for maximal extraction. This phenomena indicates that the improvement is not due to simple surface-area increase, but is related to a more complex mechanism of de-structuring of the plant. It appears that the lowest improvement was obtained in PSD under 10 microns, possibly due to over de-structuring of plant cells, or due to stripping the active ingredients in the high air streams.

Although there are some variability and inconsistency in few experimental points, the trend is rather clear. These inconsistencies (i.e. the results at 24 microns) can be explained by the variability of the feed material.

It can be therefore stated that the optimum range for PSD in this strain is: d(0.9) ~13-30 microns and that there is no further improvement when micronizing under 20 microns. The following tables show the results for the two other THC-rich strains:

TABLE 2

The effect of particle size on cannabinoids extractability TCH rich #2

| d (0.9), microns | $\Delta^9$-THC (wt/wt) % | THCA-A (wt/wt) % | Total Cannabinoids % (wt/wt) | $\Delta^9$-THC (improve) % | % improve THCA-A | % improve total |
|---|---|---|---|---|---|---|
| Original trim (about 3000 microns) | 1.04 | 4.37 | 6.3 | — | — | — |
| 62 | 1.83 | 5.68 | 8.8 | 76 | 30 | 40 |
| 58 | 2.04 | 5.82 | 9 | 96 | 33 | 43 |
| 15.7 | 1.91 | 5.79 | 8.83 | 84 | 32 | 40 |
| 12.9 | 2.03 | 6.53 | 9.85 | 95 | 49 | 56 |
| 10.2 | 1.8 | 5.64 | 8.54 | 73 | 29 | 36 |
| 7.57 | 1.43 | 5.76 | 8.26 | 38 | 32 | 31 |

TABLE 3

The effect of particle size on cannabinoids extractability TCH rich #3

| d (0.9), microns | $\Delta$9-THC (wt/wt) % | THCA-A (wt/wt) % | Total % (wt/wt) | $\Delta$9-THC (improve) % | % improve THCA-A | % improve total |
|---|---|---|---|---|---|---|
| Original trim (about 3000 microns) | 0.6 | 3.97 | 5.13 | — | — | — |
| 24.1 | 0.89 | 6.56 | 8.3 | 48.3 | 65.2 | 61.8 |
| 22.2 | 1.12 | 5.53 | 7.47 | 86.7 | 39.3 | 45.6 |
| 22 | 0.93 | 5.42 | 7.18 | 55.0 | 36.5 | 40.0 |
| 20.8 | 1.04 | 5.29 | 7.15 | 73.3 | 33.2 | 39.4 |
| 9.46 | 0.93 | 4.88 | 6.59 | 55.0 | 22.9 | 28.5 |
| 6.68 | 0.96 | 4.78 | 6.49 | 60.0 | 20.4 | 26.5 |

In both strains #2 and #3 higher improvements of 60-80% were observed. The results also show that reducing particle size below 10 microns does not improve the extractability.

Example 3

The Effect of Particle Size on Cannabinoids Extractability from Cannabis Trim of CBD-THC Balanced Strain Table 4 represents the results obtained from powder samples of various particle size prepared from the trim of a CBD-THC balanced strain. The samples were analyzed for the cannabinoids CBDA, CBD, THCA and Δ9-THC and for total cannabinoids.

TABLE 4

Cannabinoids extraction from trim of a CBD- THC-balanced strain

| $d_{90}$ (μm) | CBDA (wt/wt) % | CBD (wt/wt) % | THCA-A (wt/wt) % | Δ9-THC (wt/wt) % | Total % (wt/wt) | CBDA (improve) % | CBD (improve) % | THCA-A (improve) % | Δ9-THC (improve) % | Total % (improve) % |
|---|---|---|---|---|---|---|---|---|---|---|
| Original trim (about 3000 microns) | 1.91 | 0.32 | 1.2 | 0.42 | 4.35 | — | — | — | — | — |

TABLE 4-continued

Cannabinoids extraction from trim of a CBD- THC-balanced strain

| $d_{90}$ (μm) | CBDA (wt/wt) % | CBD (wt/wt) % | THCA-A (wt/wt) % | Δ9-THC (wt/wt) % | Total % (wt/wt) | CBDA (improve) % | CBD (improve) % | THCA-A (improve) % | Δ9-THC (improve) % | Total % (improve) % |
|---|---|---|---|---|---|---|---|---|---|---|
| 52.1 | 4.06 | 0.66 | 2.37 | 0.87 | 8.97 | 112.6 | 106.3 | 97.5 | 107.1 | 106.2 |
| 18.4 | 3.35 | 0.58 | 2.06 | 0.77 | 7.54 | 75.4 | 81.3 | 71.7 | 83.3 | 73.3 |
| 13.7 | 3.19 | 0.53 | 1.74 | 0.66 | 6.87 | 67.0 | 65.6 | 45.0 | 57.1 | 57.9 |
| 12.9 | 5.51 | 0.85 | 3.17 | 1.11 | 12.14 | 188.5 | 165.6 | 164.2 | 164.3 | 179.1 |
| 12.5 | 3.61 | 0.6 | 2.05 | 0.81 | 8.02 | 89.0 | 87.5 | 70.8 | 92.9 | 84.4 |
| 8.05 | 4 | 0.59 | 1.86 | 0.65 | 8.07 | 109.4 | 84.4 | 55.0 | 54.8 | 85.5 |

It can be seen that exceptional improvement of 2-3 tenfold was obtained. There is high variability in results so it is difficult to trace a trend in the effect of particle size, however it is clear that micronization to a value of dv(0.9) under 50 microns is sufficient to receive substantial improvement.

It can be seen that the improvement is significant. Furthermore, in the CBD-related compounds, improvement is higher than in other compounds. No trend was found for the influence of PSD. It should be noted that the absolute values of all readings are lower than in THC strains. Therefore variability in feed material is relatively higher.

CONCLUSION

Micronization process appears to clearly improve the extraction yield.

The improvement is strain dependent. The improvement can be between 30% up to 50% depend how rich is the trim.

There is an optimal PSD for maximal extraction. This phenomenon indicates that the improvement is not due to simple surface-area increase, but is related to a more complex mechanism of de-structuring of the plant.

Example 4

The Effect of Particle Size on Cannabinoids Extractability from Cannabis Flower Buds Flower buds of three different cannabis strains were studied: a CBD-rich strain, a THC-rich strain and a CBD-THC balanced strain.

Trimmed flowers were ground in a coffee grinder and sieved by a 5 mm screen. The ground flower buds were then micronized by the SuperFine vortex mill as described in Example 1 to produce powders of different PSDs. Extracts from the different powders were prepared and analyzed as described in Example 2.

However, in order to account for the variability in the feed material, extended sampling and testing for each of the strains was performed according to the following scheme: prior to grinding and sieving, three individual flowers of the same strain were divided into two sub-samples. After milling and sieving the two sub-samples were blended and the resulted blend was divided into three portions. Each portion was micronized to a different PSD in the range of 20-100 μm. Cannabinoids extractability was tested for each of the portions before micronization and for the powder prepared therefrom. Each test was duplicated.

Table 5 and Table 6 summarize the results obtained for the main peaks of the three strains prior to micronization (3 samples for each strain) and after micronization, respectively. Each result is an average of two duplicate tests. For the sake of simplicity, only the main peak in each strain are listed.

TABLE 5 results of unmicronized samples (~5 mm)

| strain | Sample | % CBDA | % THCA-A |
|---|---|---|---|
| CBD rich | 1 | 8.9 | — |
|  | 2 | 9.3 | — |
|  | 3 | 9.3 | — |
| THC rich | 1 | — | 14.3 |
|  | 2 | — | 14.6 |
|  | 3 | — | 14.4 |
| Balanced | 1 | 7.2 | 6.4 |
|  | 2 | 7.9 | 7.0 |
|  | 3 | 8.2 | 7.4 |

TABLE 6 results of micronized powders

| strain | d(0.9), microns | CBDA | THCA |
|---|---|---|---|
| CBD rich | 23.8 | 7.8 |  |
|  | 46 | 8.1 |  |
|  | 94.8 | 8.9 |  |
| THC rich | 28.3 |  | 12.7 |
|  | 37.7 |  | 13.1 |
|  | 108 |  | 13.7 |
| Balanced | 22.1 | 7.5 | 6.6 |
|  | 40.4 | 7.1 | 6.2 |
|  | 127 | 8.4 | 7.5 |

Table 7 summarizes the relative extraction improvement.

TABLE 7 change in extraction of cannabis flower buds

| | | relative change % | |
|---|---|---|---|
| Strain | d(0.9), microns | CBDA | THCA-A |
| CBD rich | 23.8 | −12.6 |  |
|  | 46 | −12.9 |  |
|  | 94.8 | −4.3 |  |
| THC rich | 28.3 |  | −11.0 |
|  | 37.7 |  | −10.7 |
|  | 108 |  | −5.17 |
| Balanced | 22.1 | 4.3 | 4.0 |
|  | 40.4 | −10.3 | −11.1 |
|  | 127 | 2.6 | 1.83 |

* relative change: 100 × [(% in micronized sample) − (% in unmicronized sample)]/(% in unmicronized sample)

As can be seen, the micronization of cannabis buds appears to impair the extraction of the main cannabinoids by only 5-10% and appears to be strain dependent. This minor decrease in extractability, as compared to the significant improvement results obtained for the trim, is possibly due to the fact that in the buds the cannabinoids are concentrated in the trichomes and protected only by thin membranes. Therefore, standard milling methods might suffice to fully extract the ingredients. Yet, a person skilled in the art would appreciate the fact that although the cannabis milling method of the invention is extremely efficient in size reduction, it does not lead to significant loss or degradation of the cannabinoid compounds, as can be seen in Tables 8. Such degradation is expected when milling is performed by conventional, more aggressive, methods. Thus, although further reduction of particle size might not be beneficial for extraction purposes, the micronized cannabis flower powders of the invention, which substantially contain all of the cannabinoids naturally present in the raw plant material, have many advantages over coarse powders when administered as is or when formulated with other ingredients in pharmaceutical products.

Tables 8A, 8B and 8C present analysis results of extraction of un-micronized and micronized powder samples of CBD rich, THC rich and CBD/THC balanced strains, respectively, showing all 15 scanned cannabinoids. The calculated relative differences between the micronized and the unmicronized samples for each of the cannabinoids are also shown. The micronized and un-micronized samples for each strain are taken from the same batch.

TABLE 8a

CBD rich flowers

| cannabinoid | % in 5 mm | % in micron. | % difference |
|---|---|---|---|
| CBDVA | 0.14 | 0.14 | 0 |
| CBDV | 0.16 | 0.16 | 0 |
| CBDA | 8.93 | 7.805 | −12.598 |
| CBGA | 0.37 | 0.375 | 1.351351 |
| CBG | 0.215 | 0.21 | −2.32558 |
| CBD | 1.55 | 1.34 | −13.5484 |
| THCV | 0 | 0 | |
| THCVA | 0 | 0 | |
| CBN | 0.15 | 0.15 | 0 |
| D9-THC | 0.25 | 0.29 | 16 |
| D8-THC | 0 | 0 | |
| CBL | 0 | 0 | |
| CBC | 0 | 0 | |
| THCA-A | 0.575 | 1.23 | 113.913 |
| CBCA | 0.51 | 0.47 | −7.84314 |

TABLE 8b

THC rich flowers

| cannabinoid | % in raw | % in micron. | % difference |
|---|---|---|---|
| CBDVA | 0.195 | 0.19 | −2.5641 |
| CBDV | 0.23 | 0.21 | −8.69565 |
| CBDA | 0.195 | 0.315 | 61.53846 |
| CBGA | 0.74 | 0.68 | −8.10811 |
| CBG | 0.25 | 0.24 | −4 |
| CBD | 0 | 0 | |
| THCV | 0 | 0.09 | |
| THCVA | 0.195 | 0.19 | −2.5641 |
| CBN | 0.165 | 0.16 | −3.0303 |
| D9-THC | 2.25 | 2.025 | −10 |
| D8-THC | 0 | 0 | |
| CBL | 0 | 0 | |
| CBC | 0 | 0 | |
| THCA-A | 14.33 | 12.74 | −11.0956 |
| CBCA | 0.275 | 0.27 | −1.81818 |

TABLE 8c

CBD/THC balanced flowers

| cannabinoid | % in raw | % in micron. | % difference |
|---|---|---|---|
| CBDVA | 0.14 | 0.135 | −3.57143 |
| CBDV | 0 | 0 | |
| CBDA | 7.19 | 7.5 | 4.311544 |
| CBGA | 0.545 | 0.55 | 0.917431 |
| CBG | 0.215 | 0.23 | 6.976744 |
| CBD | 0.42 | 0.44 | 4.761905 |
| THCV | 0 | 0 | |
| THCVA | 0.16 | 0.16 | 0 |
| CBN | 0.17 | 0.17 | 0 |
| D9-THC | 0.905 | 0.9 | −0.55249 |
| D8-THC | 0 | 0 | |
| CBL | 0 | 0 | |
| CBC | 0 | 0 | |
| THCA-A | 6.375 | 6.63 | 4 |
| CBCA | 0.485 | 0.5 | 3.092784 |

It will be realized that the cannabis powders of the invention can be optimized for their intended use by preselecting the PSD upon preparation of the powders. Thus, when a powder of the invention is intended to be used for preparing a cannabis extract, the PSD of the powder can be preselected for maximal cannabinoids extraction and/or to meet specific requirements of the desired extract composition. As demonstrates in the above Examples, optimal PSD for maximal extraction depends on the specific strain and specific plant part of the cannabis plant material. It will be also realized that extractability might also depend on the extracting solvent.

It will be appreciated by persons skilled in the art that the present invention is not limited to what has been particularly shown and described hereinabove. Rather the scope of the present invention is defined only by the claims which follow.

The invention claimed is:

1. A method for enhanced extraction of cannabis oil from a cannabis plant material, the cannabis plant material is characterized by a cannabis strain and a cannabis plant part, the method comprising:
comminuting said cannabis plant material to a powder of a preselected particle size distribution (PSD); and
extracting cannabis oil from said powder;
wherein said PSD is characterized by $10 \leq Dv(90) \leq 100$ μm as determined by laser diffraction particle size analysis; and
wherein said PSD is preselected in accordance with said cannabis strain and said plant part.

2. The method according to claim 1, wherein said comminuting comprises subjecting particles of said cannabis plant material to a flow regime comprising a vortex flow and controlled changes in air pressure and flow direction of said vortex flow, thereby said particles of said cannabis plant material break along cavities therewithin.

3. The method according to claim 2, wherein the cannabis plant material is shredded to pieces of 1-10 mm size prior to said subjecting to flow regime.

4. The method according to claim 1, wherein comminuting is performed by a vortex mill.

5. The method of claim 1, wherein said cannabis plant material is a fresh plant material.

6. The method according to claim 1, wherein said cannabis plant part is cannabis flowers.

7. The method according to claim 1, wherein said cannabis plant part is cannabis trim, said trim comprises leaves trimmed from cannabis buds and/or flowers.

8. The method according to claim 7, wherein said strain is a TCH rich strain a said PSD is characterized by $13 \leq Dv(90) \leq 30$ µm.

9. The method according to claim 7, wherein said strain is a CBD-THC-balanced strain and said PSD is characterized by $10 \leq Dv(90) \leq 50$ µm.

10. The method according to claim 1, wherein said preselected PSD is characterized by $Dv(90) \leq 100$ µm, $Dv(50) \leq 20$ µm and $Dv(10) \geq 5$ µm.

11. The method according to claim 1, wherein said preselected PSD is characterized by $Dv(90)$ in the range of 20 to 80 µm and $Dv(10) \geq 5$ µm.

12. The method according to claim 1, wherein said extracting is performed by a solvent and wherein said PSD is further preselected according to said solvent.

* * * * *

UNITED STATES PATENT AND TRADEMARK OFFICE
CERTIFICATE OF CORRECTION

PATENT NO. : 11,364,505 B2
APPLICATION NO. : 17/385949
DATED : June 21, 2022
INVENTOR(S) : Guy Samburski and Yan Beliavsky Page 1 of 1

It is certified that error appears in the above-identified patent and that said Letters Patent is hereby corrected as shown below:

On the Title Page

Item (30) Foreign Application Priority Data
Insert --Oct. 25, 2020 (IL) ............................... 278286--.

Signed and Sealed this
Thirtieth Day of September, 2025

John A. Squires
*Director of the United States Patent and Trademark Office*